United States Patent
Wang et al.

(10) Patent No.: US 6,291,627 B1
(45) Date of Patent: Sep. 18, 2001

(54) EPOXY RESIN RENDERED FLAME RETARDANT BY REACTION WITH 9,10-DIHYDRO-9-OXA-10-PHOSPHAPHENANTHRENE-10-OXIDE

(75) Inventors: Chun-Shan Wang; Ching Hsuan Lin, both of Tainan (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/437,985

(22) Filed: Nov. 10, 1999

Related U.S. Application Data

(63) Continuation-in-part of application No. 09/261,884, filed on Mar. 3, 1999.

(30) Foreign Application Priority Data

Apr. 16, 1999 (TW) .................................................. 88106160

(51) Int. Cl.⁷ .......................... C08G 59/14; C08L 63/02; C08L 63/04
(52) U.S. Cl. .......................... 528/99; 525/480; 525/481; 525/523; 525/533
(58) Field of Search ............................... 528/99; 525/480, 525/523, 533, 481

(56) References Cited

U.S. PATENT DOCUMENTS 4,618,693 * 10/1986 Saito et al. .............................. 558/82

FOREIGN PATENT DOCUMENTS 04-300968A 10/1992 (JP) .
04300968A 10/1992 (JP) .

OTHER PUBLICATIONS

Chemical abstracts accession No. 1987:138632 for Japanese Patent No. 61–236787, Sanko Chemical Co., Ltd., Oct. 22, 1986.*

Chemical abstracts accession No. 1998:329120 for the Journal of Polymer Research article by Cho et al., vol. 5, No. 2, pp. 59–65.*

Chemical abstracts accession No. 1994:410200 for Japanese Patent No. 5–331179, Sanko Kagaku KK, Dec. 14, 1993.*

Chemical abstracts accession No. 1998:488426 for the Polymer Buletin article by Cho et al., vol. 41, No. 1, pp. 45–52.*

Chun–Shan Wang and Jeng–Yueh Shieh, "Synthesis and Properties of Epoxy Resins Containing 2–(6–oxid–6H–dibenz<c,e><1,2>oxaphosphorin–6–yl) 1,4–benzenediol," Polymer vol. 39, No. 23, pp. 5819–5826, Nov. 1998.

* cited by examiner

*Primary Examiner*—Robert E. L. Sellers
(74) *Attorney, Agent, or Firm*—Jackson Walker L.L.P.

(57) ABSTRACT

A flame-retardant epoxy resin was prepared by reacting an active-hydrogen-containing phosphorus compound with a di- or poly-functional epoxy resin via an addition reaction between the active hydrogen and the epoxide group, is suitable for printed circuit board and semiconductor encapsulation applications. The active-hydrogen-containing phosphorus compound is 9,10-dihydro-9-oxa-10-phosphaphenanthrene 10-oxide having a chemical structure as follows:

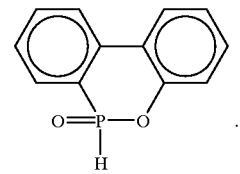

16 Claims, No Drawings

EPOXY RESIN RENDERED FLAME RETARDANT BY REACTION WITH 9,10-DIHYDRO-9-OXA-10-PHOSPHAPHENANTHRENE-10-OXIDE

CROSS-REFERENCE TO RELATED APPLICATION

The present application is a continuation-in-part application of U.S. patent application Ser. No. 09/261,884, field Mar. 3, 1999 pending.

The above-listed application Ser. No. 09/261,884 is commonly assigned with the present invention and the entire content of which is incorporated herein by reference.

FIELD OF THE INVENTION

The present invention relates generally to flame-retardant epoxy resins prepared by reacting an active-hydrogen-containing phosphorus compound with a di- or poly-functional epoxy resin via an addition reaction between the active hydrogen and the epoxide group. The present invention also relates to cured epoxy resins resulting from the epoxy resins, which have excellent flame-retardancy and mechanical properties.

BACKGROUND OF THE INVENTION

Epoxy resins have the excellent characteristics of moisture, solvent and chemical resistance, toughness, low shrinkage on cure, superior electrical and mechanical resistance properties, and good adhesion to many substrates. The versatility in formulation also make epoxy resins widely applicable industrially for surface coatings, adhesive, painting materials, potting, composites, laminates, encapsulants for semiconductors, and insulating materials for electric devices, etc. o-Cresol formaldehyde novolac epoxy (CNE) is the resin typically employed in the encapsulation of microelectronic devices. Several approaches for modification of epoxy backbone for enhancing the thermal properties of epoxy resins have been reported. Aromatic bromine compounds in conjunction with antimony oxide are widely used as a flame retardant for epoxy resins. Tetrabromobisphenol A is a typical example of the aromatic bromine compounds used as a flame retardant for epoxy resins. An excess amount of epoxy resin is reacted with tetrabromobisphenol A to prepare an advanced epoxy resin having two terminal epoxide groups, as shown in the following formula:

A flame retardant advanced epoxy resin wherein EP is a bi-radical group of the backbone of the epoxy resin, and m is an integer of 1–10. The advanced epoxy resin can be used in preparing a flame-retardant printed circuit board (FR-4) by impregnating glass fibers with the advanced epoxy resin and heating the resulting composite to cure the advanced epoxy resin. Furthermore, the advanced epoxy resin can be employed to encapsulate microelectronic devices, in which the advanced epoxy resin is cured at a high temperature with a curing agent, so that an encapsulant having a flame-retardant property is formed. Typical examples can be found in U.S. Pat. No. 3,040,495 (1961); U.S. Pat. No. 3,058,946 (1962); U.S. Pat. No. 3,294,742 (1966); U.S. Pat. No. 3,929,908 (1975); U.S. Pat. No. 3,956,403 (1976); U.S. Pat. No. 3,974,235 (1976); U.S. Pat. No. 3,989,531 (1976); U.S. Pat. No. 4,058,507 (1997); U.S. Pat. No. 4,104,257 (1978); U.S. Pat. No. 4,170,711 (1979); and U.S. Pat. No. 4,647,648(1987)].

Although the tetrabromobisphenol A-containing advanced epoxy resin shows flame retardant property, major problems encountered with this system are concerned with the generation of toxic and corrosive fumes during combustion such as dioxin and benzofuran.

The flame retardant having a small molecular weight tends to degrade the mechanical properties of the epoxy resins, and migrate/vaporize from the epoxy resins such that the flame retardancy thereof diminishes.

Owing to organic phosphorus compounds generate less toxic gas and smoke than halogen-containing compounds, some authors have reported advanced epoxy resins containing phosphorus compound [Japanese patent application publication No. 10-30017 (1998), Japanese patent application publication No. 10-30016 (1998), Japanese patent application publication No. 10-152545 (1998)]. One example of the reaction is shown in the following scheme [Japanese patent application publication No. 10-30017 (1998)]:

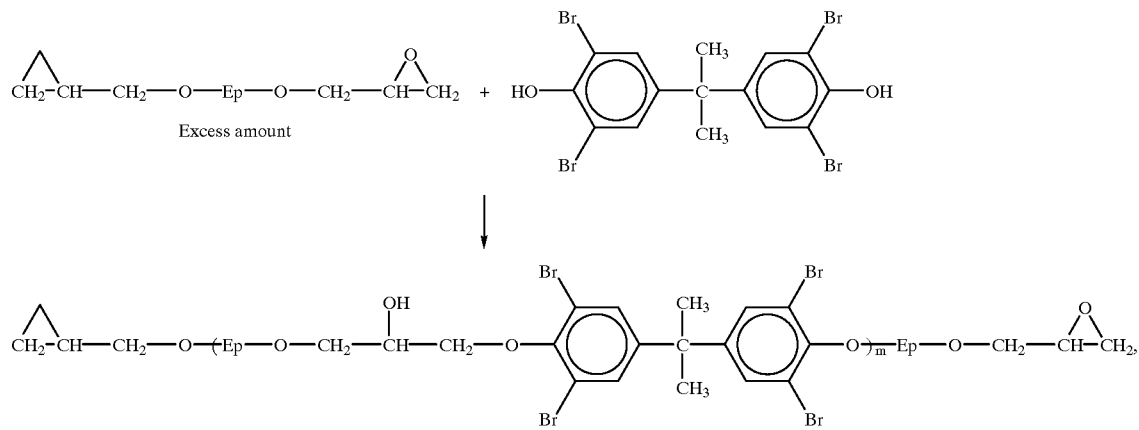

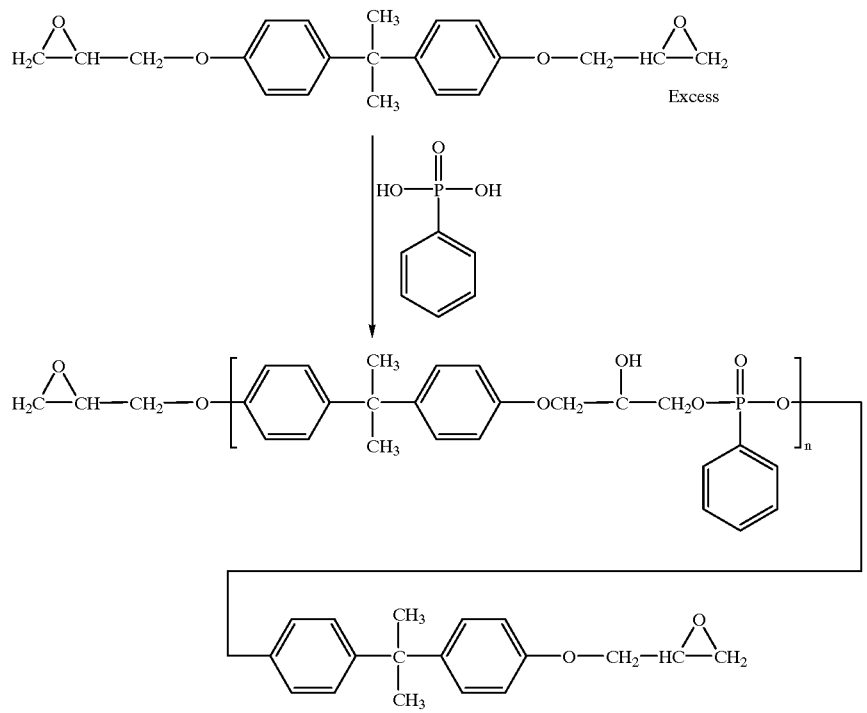

Although these phosphorus containing advancement epoxy resins exhibited good flame retardancy, they were all derived from the reaction between aromatic phenol and epoxy group. For a multifuntional epoxy resin (functionality>2), this advancement reaction may lead to gel if the reaction is not controlled well. These advancement epoxy resins yield low Tg product because they are derived from difunctional DGEBA (diglycidyl ether bisphenol A epoxy resin) and also due to their high EEW (epoxide equivalent weight) (EEW>400 g/eq). In order to increase their Tg (glass transition temperature), multifunctional epoxy resin has to be added into these advanced resins. The blending of a multifunctional epoxy into these advanced resins may result in phase separation due to the difference in the reactivity between the multifuntional epoxy resin and the advanced epoxy resin toward the curing agent.

The trend of electronics equipment is being miniaturized and becoming thinner, at the same time the scale of integration of large scale integrated circuits (LSICs) is continuing upward, forcing the design toward larger chips, finer patterns, and higher pin counts that are more susceptible to a high-temperature failure. The prevailing surface mount technology (SMT) also causes the devices being subjected to a high temperature. Therefore, the development of a high-temperature reliable, flame-retardant and environmentally friendly epoxy resin for printed circuit board and encapsulant are essential for semiconductor industry.

It is an object of this invention to provide flame retardant advanced epoxy resins and cured epoxy resins with good thermal stability, superior heat resistance, and environment friendly, which are suitable for use in making printed circuit boards and in semiconductor encapsulation applications.

It is another object of this invention to provide a method for improving flame retardant properties of epoxy resins.

SUMMARY OF THE INVENTION

In order to accomplish the aforesaid objects, a flame retardant epoxy resin and a cured epoxy resin were synthesized in the prevent invention.

The flame-retardant epoxy resin was prepared by reacting a phosphorus-containing compound having an active hydrogen connected directly to the phosphorus atom with a di- or poly-functional epoxy resin via an addition reaction between the active hydrogen and the epoxide group. The flame-retardant cured epoxy resin prepared from this epoxy resin has a high glass transition temperature (Tg), high decomposition temperature and high elastic modulus, and is free of toxic and corrosive fumes during combustion, and thus is suitable for printed circuit board and semiconductor encapsulation applications. The active-hydrogen-containing phosphorus compound is 9,10-dihydro-9-oxa-10-phosphaphenanthrene 10-oxide having a chemical structure (I) as follows:

(I)

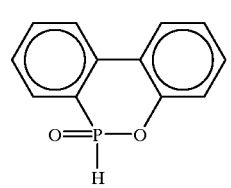

DETAILED DESCRIPTION OF THE INVENTION

A phosphorus-containing flame-retardant epoxy resin prepared in accordance with the present invention has a structure selected from the group consisting of formulas (a) to (d):

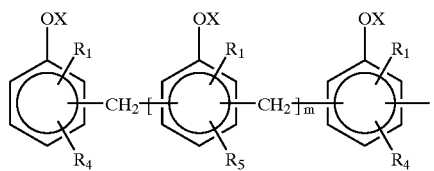
(a)

wherein:

m is an integer from 1 to 12; $R_1$=H or $C_1$–$C_4$ hydrocarbon radical; $R_4$ and $R_5$ are, independently, hydrogen, methyl or

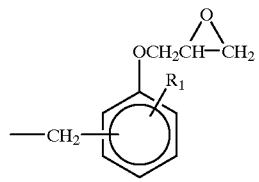

wherein $R_1$ is defined as above; and
X=A or B, and at least one of X is B, wherein

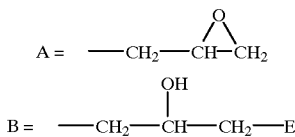

wherein E is

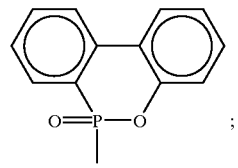

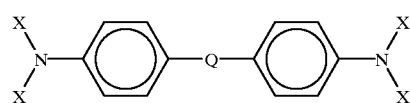
(b)

wherein X is defined as above; and Q is

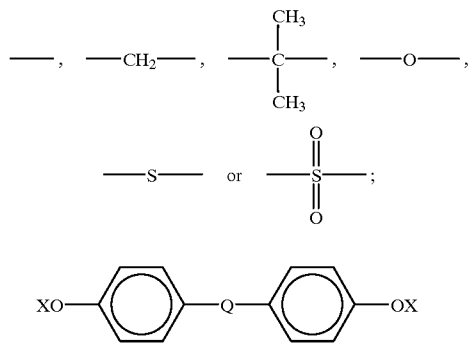

(c)

wherein X and Q are defined as above; and

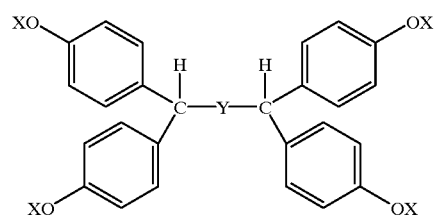
(d)

wherein X is defined as above; and Y is —$(CH_2)_n$— or phenylene, wherein n is an integer of 0 to 6.

Preferably, the flame-retardant epoxy resin has the formula (a), and $R_1$ is hydrogen, —$CH_3$, and $R_4$ is hydrogen.

Preferably, the flame-retardant epoxy resin has the formula (c), and Q is —$C(CH_3)_2$—.

Preferably, the flame-retardant epoxy resin contains 1–30 wt %, and more preferably, 1–10 wt % phosphorus.

A suitable process for preparing the phosphorus-containing flame-retardant epoxy resin of the present invention comprises reacting an active-hydrogen-containing phosphorus compound, (9,10-dihydro-9-oxa-10-phosphaphenanthrene 10-oxide, DOPO), having the following formula (I)

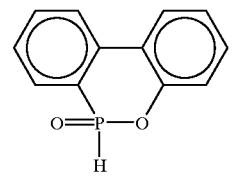
(I)

with an epoxy resin having a formula selected from the group consisting of (a') to (d') in a molten state or in a common solvent and without or in the presence of a catalyst:

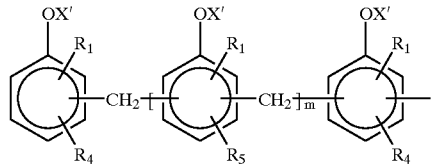
(a')

wherein:

m is an integer and 0<m<12; $R_1$=H or $C_1$–$C_4$ hydrocarbon radical; $R_4$ and $R_5$ independently are hydrogen, methyl or

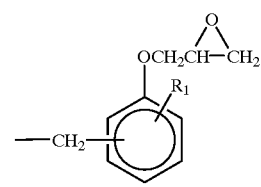

wherein $R_1$ has the same definition as above; and $$X' = -CH_2-CH-CH_2;$$
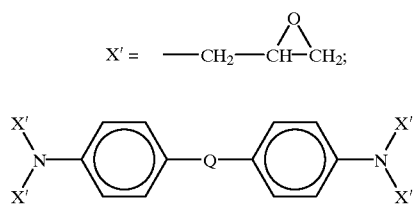

(b')

wherein X' is defined the same as above; and Q is

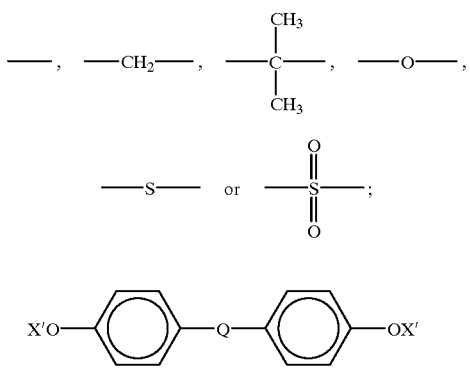

(c')

wherein X' and Q are defined as above; and

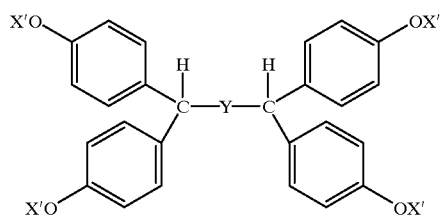

(d')

wherein X' is defined as above; and Y is $-(CH_2)_n-$ or phenylene, wherin n is an integer of 0 to 6.

In the process for preparing the phosphorus-containing flame-retardant epoxy resin of the present invention, the active hydrogen of the phosphorus compound, DOPO, reacts with the epoxide groups of the epoxy resin via an addition reaction, as shown in the following scheme (II), and thus both a di- and poly-functional epoxy resin can be used in the present invention.

(II)

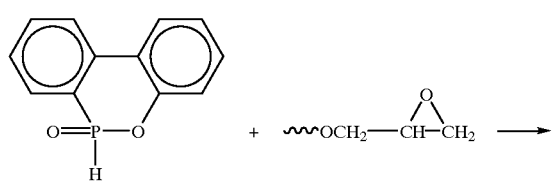

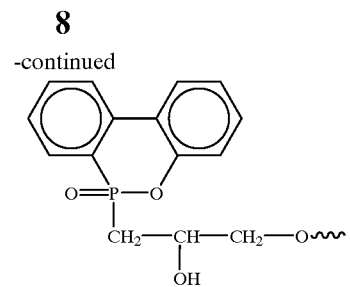

Preferably, the reaction (II) is carried out at 100° C.–200° C., and with an equivalent ratio of the epoxide group in the epoxy resin (selected from (a') to (d')) to the active hydrogen connected to the phosphorous in the phosphorus-containing compound (I) ranging from 2:1 to 10:1. This reaction (II) may be carried out in the presence of a catalyst selected from the group consisting of 2-phenylimidazole, 2-methylimidazole, triphenylphosphine, a quarternary phosphoium compound and a quarternary ammonium compound. Examples of the quarternary phosphoium compound include ethyltriphenyl phosphonium acetate and ethyltriphenyl phosphonium halides. Examples of the quarternary ammonium compound are benzyltrimethyl ammonium chloride, benzyltriethyl ammonium chloride and tetrabutyl ammonium chloride.

The flame-retardant epoxy resin prepared in the present invention can be used in preparing a flame-retardant printed circuit board (FR-4) as a matrix resin by impregnating glass fibers with the advanced flame-retardant epoxy resin and curing the resulting composite.

The present invention further synthesized a phosphorus-containing flame-retardant cured epoxy resin by curing the phosphorus-containing flame-retardant epoxy resin of the present invention with a curing agent of an epoxy resin. The curing agent can be any curing agent used in the art for curing an epoxy resin, and preferably is selected from the group consisting of phenol-formaldehyde novolac, dicyandiamide, methylenedianiline, diaminodiphenyl sulfone, phthalic anhydride and hexahydrophthalic anhydride. Preferably, the curing reaction is carried out at a temperature higher than 150° C. and with a stoichiometric amount of the curing agent, i.e. the equivalent ratio of the epoxide group in the advance epoxy resin and the functional groups in the curing agent is about 1:1. More preferably, the curing reaction is carried out in the presence of a curing promoter such as triphenylphosphine, and in an amount of 0.01–10.0 parts by weight of the curing promoter per 100 parts by weight of the advance epoxy resin. The phosphorus-containing flame-retardant cured epoxy resin of the present invention is suitable for use in semiconductor encapsulation.

A suitable epoxy resin for use in the present invention can be any known epoxy resin, for examples those having two epoxide groups such as bisphenol A epoxy resin, bisphenol F epoxy resin, bisphenol S epoxy resin and biphenol epoxy resin, and those having more than two epoxide groups such as phenol formaldehyde novolac epoxy and cresol formaldehyde novolac epoxy (CNE) with 4–18 functional groups, and mixtures thereof.

I. Preparation of Phosphorus-containing Flame-Retardant Epoxy Resin

EXAMPLE 1

Epoxy Resin IIP$_1$ (Phosphorus Content 1 wt %) Prepared from Diglycidyl Ether of Bisphenol A (DGEBA) and DOPO To a one liter four-neck round-bottom flask equipped with a heating mantle, a thermocouple and temperature controller, a reflux condenser, a nitrogen feed, a vacuum system and a mechanical stirrer, 700 g diglycidyl ether of bisphenol A (DGEBA) having an epoxide equivalent weight (EEW) of 187 g/eq was added, and heated to 110° C. while stirring and vacuuming (<100 mmHg) for a period of 30 minutes to remove a trace amount of water contained in the epoxy resin. The vacuuming was stopped, and dried nitrogen was introduced into the flask until the atmospheric pressure was reached. The temperature of the flask was raised to 130° C., and 52.5 g of 9,10-dihydro-9-oxa-10-phosphaphenanthrene-10-oxide (DOPO, purchased from TCI) was then added while stirring. The temperature of the reaction mixture was gradually increased to 160° C. and maintained at that temperature for five hours. A phosphorus containing epoxy resin IIP$_1$ with EEW 215 g/eq was obtained after cooling (216 g/eq theoretically).

EXAMPLE 2–3

Preparation of Epoxy Resins IIP$_2$ (Phosphorus Content 2 wt %) and IIP$_3$ (Phosphorus Content 3 wt %)

The procedures described in Example 1 were repeated, except that the amount of DOPO was changed to 113.5 g and 185 g in Examples 2 and 3, respectively. The resultant product IIP$_2$ (Example 2) has a phosphorus content of 2 wt % and EEW of 252 g/eq (252 g/eq theoretically). The resultant product IIP$_3$ (Example 3) has a phosphorus content of 3 wt % and EEW of 308 g/eq (306 g/eq theoretically).

EXAMPLE 4

Epoxy Resin C$_{12}$P$_2$ (Phosphorus Content 2 wt %) Prepared from Cresol Formaldehyde Novolac Epoxy Resin (CNE) and DOPO To a one liter four-neck round-bottom flask equipped with a heating mantle, a thermocouple and temperature controller, a reflux condenser, a nitrogen feed, a vacuum system and a mechanical stirrer, 400 g cresol formaldehyde novolac epoxy resin (CNE, available from Nan Ya Plastics Co., Taiwan, under a code name of NPCN-704) having an epoxide equivalent weight (EEW) of 205 g/eq and functionality of 12 was added, and heated to 110° C. while stirring and vacuuming (<100 mmHg) for a period of 30 minutes to remove a trace amount of water contained in the epoxy resin. The vacuuming was stopped, and dried nitrogen was introduced into the flask until the atmospheric pressure was reached. The temperature of the flask was raised to 130° C., and 68 g of 9,10-dihydro-9-oxa-10-phosphaphenanthrene-10-oxide (DOPO, purchased from TCI) was then added while stirring. The temperature of the reaction mixture was gradually increased to 160° C. and maintained at that temperature for 2.5 hours. A phosphorus containing advanced epoxy resin C$_{12}$P$_2$ with EEW 275 g/eq was obtained after cooling (285 g/eq theoretically).

EXAMPLE 5

Preparation of Epoxy Resin C$_{12}$P$_4$ (Phosphorus Content 4 wt %)

The procedures described in Example 4 were repeated, except that the amount of DOPO was changed to 155 g. The resultant product C$_{12}$P$_4$ has phosphorus content of 4 wt % and EEW of 485 g/eq (464 g/eq theoretically).

The reaction in Examples 4 and 5 is shown as follows:

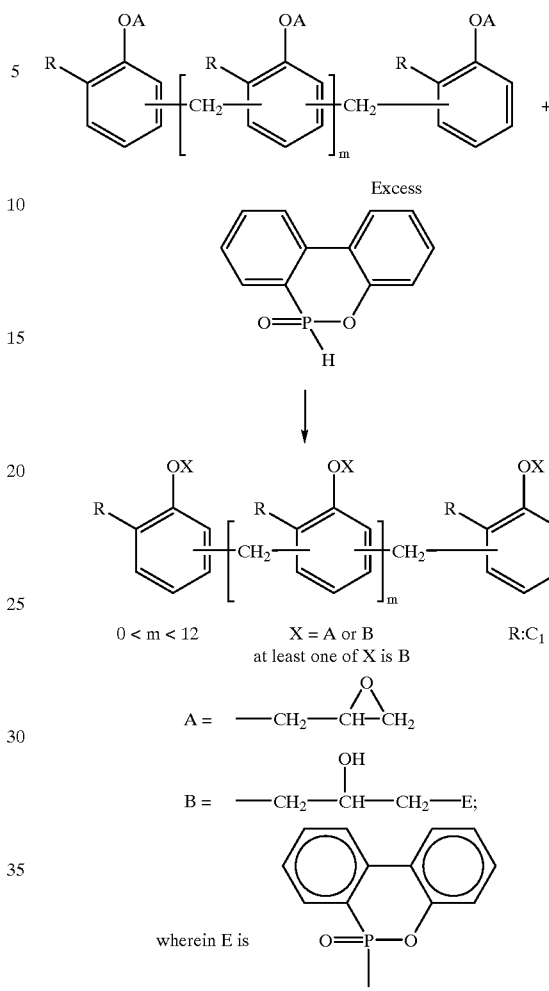

II. Curing of the Epoxy Resins

Cured epoxy resins were prepared separately from the epoxy resins prepared in Examples 1–5, DGEBA (control) and CNE (control) with a curing agent in a 1:1 equivalent ratio. The curing agent was selected from diaminodiphenyl sulfone (DDS), phenol-formaldehyde novolac having an OH equivalent weight of 105 g/eq (PN) or dicyandiamide (DICY). The mixture was grounded into fine powder and then heated on a hot plate at about 150° C. with a continuous stirring until a homogenous solution was obtained. DDS and DICY curing systems did not require a curing accelerator, but for PN curing system, 0.2 wt % of triphenylphosphine was added and stirred prior to heating. The homogenous solution was poured into an aluminum mold and then cured in an oven.

For the epoxy resins prepared from DGEBA (Examples 1–3) and the pure DGEBA epoxy resin (control) the curing was conducted at 160° C. for one hour, and 180° C. for four hours. For the epoxy resins prepared from CNE (Examples 4–5) the curing was conducted at 160° C. for one hour, 180° C. for two hours and 200° C. for two hours. Additional two hours at 200° C. was applied for the pure CNE epoxy resin (control). The samples were allowed to cool slowly to room temperature in order to prevent cracking.

The dynamic mechanical analysis (DMA) properties of the resulting cured epoxy resins in Examples 1–3 and the control (DGEBA) are shown in Table 1; the thermogravimetric analysis data thereof are shown in Table 2; and the flame-retardant properties thereof are shown in Table 3.

TABLE 1

DMA properties

| Samples | Glass transition temperature (Tg, ° C.) | Modulus 50° C., × $10^8$ Pa |
| --- | --- | --- |
| DGEBA/DDS | 190 | 18.8 |
| $IIP_1$/DDS | 188 | 19.2 |
| $IIP_2$/DDS | 155 | 20.4 |
| $IIP_3$/DDS | 124 | 18.1 |
| DGEBA/PN | 151 | 16.4 |
| $IIP_1$/PN | 134 | 18.4 |
| $IIP_2$/PN | 129 | 21.3 |
| $IIP_3$/PN | 117 | 17.7 |

TABLE 2

TGA data

| Samples | Td 5% ° C. $N_2$ | Td 5% ° C. Air | Char yield at 700° C. (%) $N_2$ | Char yield at 700° C. (%) Air |
| --- | --- | --- | --- | --- |
| DGEBA/DDS | 405 | 379 | 15.1 | 0 |
| $IIP_1$/DDS | 388 | 375 | 15.93 | 4 |
| $IIP_2$/DDS | 386 | 363 | 17.64 | 11.3 |
| $IIP_3$/DDS | 375 | 356 | 20 | 18.7 |
| DGEBA/PN | 423 | 417 | 19.1 | 0 |
| $IIP_1$/PN | 396 | 386 | 22.5 | 15.9 |
| $IIP_2$/PN | 371 | 383 | 25 | 19.5 |
| $IIP_3$/PN | 366 | 364 | 26.9 | 20.7 |

TABLE 3

UL-94 test and LOI (limiting oxygen index) measurement

| | | UL-94 test | | | |
| --- | --- | --- | --- | --- | --- |
| Samples | P % | 1st burning time[a] | 2nd burning time[a] | UL-94 grade | LOI |
| DGEBA/DDS | 0 | >60 | — | V-2 | 22 |
| $IIP_1$/DDS | 0.78 | 9.5 | 5.3 | V-1 | 25 |
| $IIP_2$/DDS | 1.60 | 6.3 | 3.1 | V-0 | 28 |
| $IIP_3$/DDS | 2.49 | 2.1 | 0.9 | V-0 | 30 |
| DGEBA/PN | 0 | >80 | — | HB[b] | 21 |
| $IIP_1$/PN | 0.67 | 53 | — | V-2 | 23 |
| $IIP_2$/PN | 1.41 | 19.2 | 4.5 | V-1 | 25 |
| $IIP_3$/PN | 2.23 | 2.1 | 1.1 | V-0 | 27 |

[a]the burning time (sec) after they are fired for 10 sec.
[b]heavy burning

The dynamic mechanical analysis (DMA) properties of the resulting cured epoxy resins in Examples 4–5 and the control (CNE) are shown in Table 4; the thermogravimetric analysis data thereof are shown in Table 5; and the flame-retardant properties thereof are shown in Table 6.

TABLE 4

DMA properties

| Samples | Glass transition temperature (Tg, ° C.) | Modulus 50° C., × $10^8$ Pa |
| --- | --- | --- |
| CNE/DDS | 255 | 1.02 |
| $C_{12}P_2$/DDS | 228 | 1.06 |
| $C_{12}P_4$/DDS | 178 | 1.05 |
| CNE/PN | 216 | 2.12 |
| $C_{12}P_2$/PN | 178 | 2.89 |
| $C_{12}P_4$/PN | 155 | 2.37 |
| CNE/DICY | 248 | 1.23 |
| $C_{12}P_2$/DICY | 213 | 1.78 |
| $C_{12}P_4$/DICY | 169 | 1.25 |

TABLE 5

TGA data

| Samples | Td 5% ° C. $N_2$ | Td 5% ° C. Air | Char yield at 700° C. (%) $N_2$ | Char yield at 700° C. (%) Air |
| --- | --- | --- | --- | --- |
| $C_{12}$/DDS | 407 | 416 | 29.9 | 0 |
| $C_{12}P_2$/DDS | 386 | 387 | 42.3 | 25 |
| $C_{12}P_4$/DDS | 371 | 374 | 43.6 | 29.5 |
| $C_{12}$/PN | 407 | 408 | 40.1 | 0 |
| $C_{12}P_2$/PN | 391 | 394 | 47.6 | 35 |
| $C_{12}P_4$/PN | 376 | 378 | 46.7 | 41 |
| $C_{12}$/DICY | 373 | 380 | 29.3 | 2.2 |
| $C_{12}P_2$/DICY | 363 | 370 | 33.7 | 21.4 |
| $C_{12}P_4$/DICY | 364 | 370 | 35.0 | 27.9 |

TABLE 6

UL-94 test and LOI (limiting oxygen index) measurement

| Samples | P % | Drip or not | Fume or not | Grade | LOI |
| --- | --- | --- | --- | --- | --- |
| $C_{12}$/DDS | 0 | Yes | Yes | V-2 | 23 |
| $C_{12}P_2$/DDS | 1.69 | No | No | V-0 | 27 |
| $C_{12}P_4$/DDS | 3.63 | No | No | V-0 | 33 |
| $C_{12}$/PN | 0 | Yes | No | V-2 | 21 |
| $C_{12}P_2$/PN | 1.45 | No | No | V-0 | 26 |
| $C_{12}P_4$/PN | 3.29 | No | No | V-0 | 28 |
| $C_{12}$/DICY | 0 | Yes | No | V-2 | 24 |
| $C_{12}P_2$/DICY | 1.86 | No | No | V-0 | 34 |
| $C_{12}P_4$/DICY | 3.83 | No | NO | V-0 | 38 |

Tables 1 to 6 show that the cured epoxy resins of the present invention have good mechanical and thermal properties, and have excellent flame retardant properties, especially no fume and dripping occur in the combustion test, and thus are very suitable for the printed circuit board fabrication, semiconductor encapsulation and other industrial applications.

In the other embodiments of the present invention, the procedures of Examples 4 and 5 were repeated except that a cresol formaldehyde novolac epoxy resin of NPCN-703 (CNE, available from Nan Ya Plastics Co., Taiwan) having a functionality of 8 was used to replace the NPCN-704 CNE. Similar results were obtained in comparison with those shown in Tables 4 to 6.

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A phosphorus-containing flame-retardant epoxy resin having a structure selected from the group consisting of formulas (a) to (d):

(a)

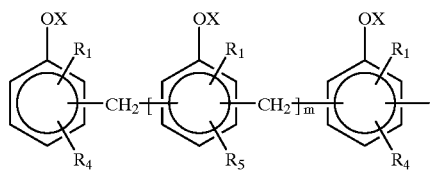

wherein:

m is an integer from 1 to 12; $R_1$=H or $C_1$–$C_4$ hydrocarbon radical $R_4$ and $R_5$ are, independently, hydrogen, methyl or

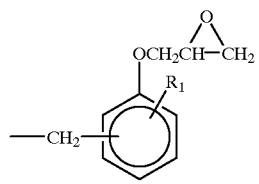

wherein $R_1$ is defined as above; and
X=A or B, and at least one of X is B, wherein

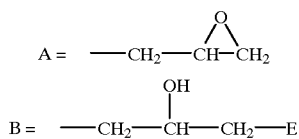

wherein E is

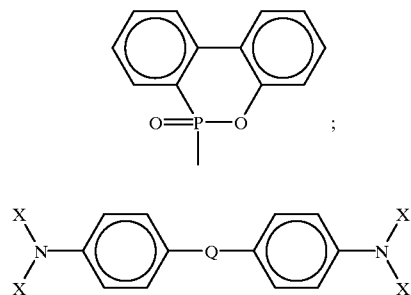

(b)

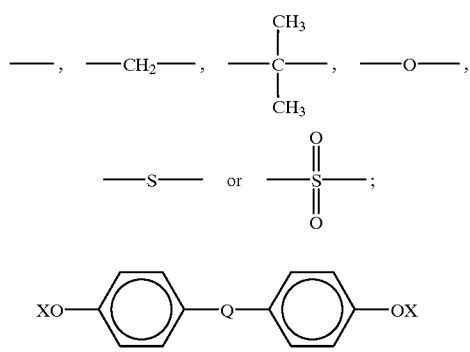

wherein X is defined as above; and Q is

—, —$CH_2$—, —$\overset{\underset{\displaystyle CH_3}{|}}{\underset{|}{C}}$—, —O—, $CH_3$ —S— or —$\overset{\overset{\displaystyle O}{\|}}{\underset{\underset{\displaystyle O}{\|}}{S}}$—;

(c)

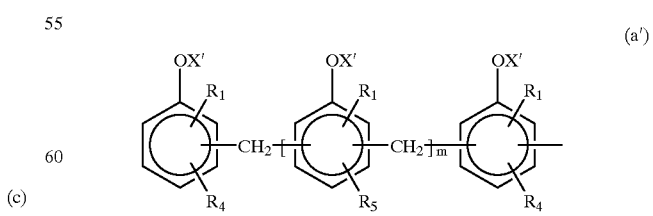

wherein X and Q are defined as above; and (d)

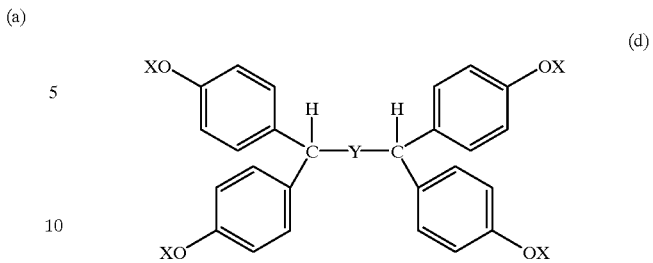

wherein X is defined as above; and Y is —($CH_2$)$_n$— or phenylene, wherein n is an integer of 0 to 6.

2. The flame-retardant epoxy resin according to claim 1, wherein the flame-retardant advanced epoxy resin has the formula (a), and $R_1$ is hydrogen or —$CH_3$, and $R_4$ is hydrogen.

3. The flame-retardant epoxy resin according to claim 2, wherein the flame-retardant advanced epoxy resin contains 1–30 wt % phosphorus.

4. The flame-retardant epoxy resin according to claim 3, wherein the flame-retardant advanced epoxy resin contains 1–10 wt % phosphorus.

5. The flame-retardant epoxy resin according to claim 1, wherien the flame-retardant advanced epoxy resin has the formula (c), and Q is —C($CH_3$)$_2$—.

6. The flame-retardant epoxy resin according to claim 5, wherein the flame-retardant advanced epoxy resin contains 1–30 wt % phosphorus.

7. The flame-retardant epoxy resin according to claim 6, wherein the flame-retardant advanced epoxy resin contains 1–10 wt % phosphorus.

8. A process for preparing the phosphorus-containing flame-retardant epoxy resin of claim 1 comprising reacting an active-hydrogen-containing phosphorus compound, 9,10-dihydro-9-oxa-10-phosphaphenanthrene 10-oxide, having the following formula (I)

(I)

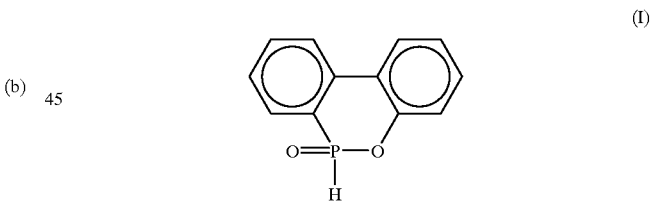

with an epoxy resin having a formula selected from the group consisting of (a') to (d') in a molten state or in a common solvent and without or in the presence of a catalyst:

(a')

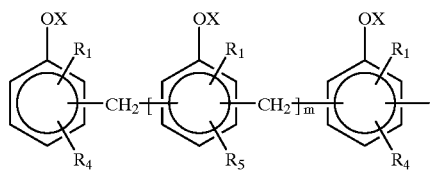

wherein:

m is an integer and 0<m<12; $R_1$=H or $C_1$–$C_4$ hydrocarbon radical; $R_4$ and $R_5$ independently are hydrogen, methyl or

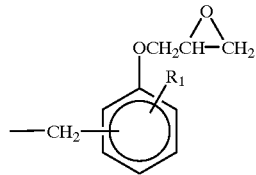

wherein $R_1$ has the same definition as above; and

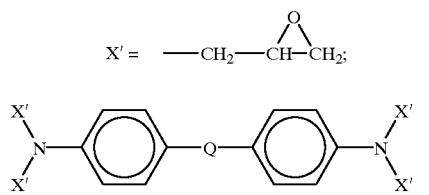

wherein X' is defined the same as above; and Q is

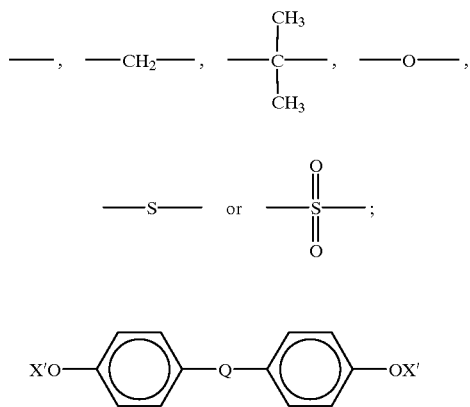

wherein X' and Q are defined as above; and

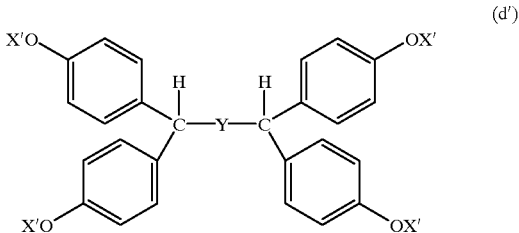

wherein X' is defined as above; and Y is —$(CH_2)_n$— or phenylene, wherin n is an integer of 0 to 6.

9. The process according to claim 8, wherein the reaction is carried out at 100° C.–200° C., and with an equivalent ratio of an epoxide group in the epoxy resin to an active hydrogen connected to the phosphorus in the phosphorus-containing compound (I) ranging from 2:1 to 10:1.

10. The process according to claim 8, wherein the reaction is carried out in the presence of a catalyst selected from the group consisting of 2-phenylimidazole, 2-methylimidazole, triphenylphosphine, a quarternary phosphonium compound and a quarternary ammonium compound.

11. The process according to claim 8, wherein the epoxy resin has the formula (a'), and $R_1$ is hydrogen or —$CH_3$, and $R_4$ is hydrogen.

12. The process according to claim 11, wherein the resulting phosphorus-containing flame-retardant epoxy resin contains 1–30 wt % phosphorus.

13. The process according to claim 12, wherein the resulting flame-retardant epoxy resin contains 1–10 wt % phosphorus.

14. The process according to claim 8, wherein the epoxy resin has the formula (c'), and Q is —$C(CH_3)_2$—.

15. The process according to claim 14, wherein the resulting flame-retardant epoxy resin contains 1–30 wt % phosphorus.

16. The process according to claim 15, wherein the resulting flame-retardant epoxy resin contains 1–10 wt % phosphorus.

* * * * *